United States Patent [19]

Dodson et al.

[11] Patent Number: 5,205,816
[45] Date of Patent: Apr. 27, 1993

[54] LAPAROSCOPIC IRRIGATOR-ASPIRATOR BLUNT DISSECTOR

[75] Inventors: Donald Dodson, Fort Worth, Tex.; Rand J. Podell, Marietta, Ga.; James B. Elder, Fort Worth; Joseph A. Staley, Jr., Roanoke, both of Tex.

[73] Assignee: O. R. Concepts, Inc., Roanoke, Tex.

[21] Appl. No.: 867,553

[22] Filed: Apr. 13, 1992

[51] Int. Cl.$^5$ .............................................. A61M 35/00
[52] U.S. Cl. ............................................. 604/1; 604/2; 604/3; 128/751
[58] Field of Search .................. 606/190; 604/1–3, 604/22; 128/750–752, 757–759

[56] References Cited

U.S. PATENT DOCUMENTS

| | | |
|---|---|---|
| 1,114,268 | 10/1914 | Kells . |
| 2,490,168 | 12/1949 | Strauss .................... 604/2 |
| 2,701,559 | 2/1955 | Cooper . |
| 2,839,049 | 6/1958 | MacLean . |
| 3,520,300 | 7/1970 | Flower, Jr. . |
| 3,542,025 | 11/1970 | Gustafson .................... 604/1 |
| 3,963,028 | 6/1976 | Cooley et al. . |
| 4,027,659 | 6/1977 | Slingluff . |
| 4,233,025 | 11/1980 | Larson et al. ................ 604/1 |
| 4,477,256 | 10/1984 | Hirsch . |
| 4,958,621 | 9/1990 | Topel et al. . |
| 5,022,414 | 6/1991 | Muller . |
| 5,031,635 | 7/1991 | Koll . |

FOREIGN PATENT DOCUMENTS

WO89/00403 1/1989 PCT Int'l Appl. .

OTHER PUBLICATIONS

Marshburn and Hulka, A Simple Irrigator-Aspirator Cannula for Laparoscopy: The Stewart System, *Obstetrics & Gynecology*, vol. 75, No. 3, Part 1, Mar. 1990, pp. 458–460.

Baer, Maddern and Blumgart, New Water-Jet Dissector: Initial Experience in Hepatic Surgery, *Br. J. Surg.* 1991, vol. 78, Apr., 502–503.

Endoscopic Kittner Blunt Dissecting Instrument advertising page, O.R. Concepts, Inc., Roanoke, Tex., May 29, 1991.

Kipfmuller et al., Endoscopic Microsurgical Dissection of the Esophagus, *Surgical Endoscopy* (1989)3:63–69.

*Primary Examiner*—Stephen C. Pellegrino
*Assistant Examiner*—Gary Jackson
*Attorney, Agent, or Firm*—Randall C. Brown; Jeffrey M. Becker

[57] ABSTRACT

A laparoscopic medical instrument for performing blunt dissection, as well as irrigation and aspiration of the operative field. The instrument comprises an elongated suction tube having proximal and distal ends, with the proximal end connected to a source of irrigation fluid and to vacuum suction equipment. A cannulated mandrel is partly inserted into the distal end leaving a portion of the mandrel extending outwardly from the elongated tube. A strip of cloth having a textured surface is wound around the outwardly extending portion of the mandrel for performing blunt dissection. An inner tube extends within the mandrel such that the bore of the inner tube is in registry with the bore of the elongated tube to provide a continuous internal bore extending through the entire instrument for supplying irrigation fluid and for removing the fluid and debris during aspiration. An X-ray opaque strip is wound within the cloth strip.

8 Claims, 1 Drawing Sheet

LAPAROSCOPIC IRRIGATOR-ASPIRATOR BLUNT DISSECTOR

BACKGROUND OF THE INVENTION

1. Field of the Invention

The present invention relates in general to a medical instrument for use in laparoscopic surgery. More particularly, the invention relates to a laparoscopic instrument which functions as an irrigator, an aspirator and a blunt dissector.

2. Description of the Prior Art

During a surgical procedure, several layers of tissue must usually be penetrated to reach the operative field. When excising an organ, such as a gallbladder, the tissue surrounding the organ must be penetrated before the organ can be removed. The removal or tearing of such tissue is known as dissection. The tissues being dissected, however, often contain blood vessels, nerves, lymph vessels, and the like, which must not be severed. The technique of blunt dissection is often used to prevent unnecessary damage caused by severing these vessels or nerves.

Blunt dissection, as opposed to sharp dissection, involves the use of a blunt surface to break through the tissue, thereby preventing the damage and bleeding caused by lasers and scapels, the tools of sharp dissection. Hard surgical sponges, generally known as peanuts or Kittner sponges, or a surgeon's fingers are often used as blunt dissectors. A peanut is a tightly wound ball of absorbent material, such as gauze or other woven cotton, which typically is gripped with forceps. The weave of the material acts to abrade the tissue being dissected so that the dissection can be performed by either pulling on the tissue or by forcing the peanut through the tissue.

Laparoscopy, surgery performed through several small incisions made in the body rather than through a single large opening, is quickly becoming the preferred method of performing certain procedures due to the reduced trauma and risk of infection as compared to normal surgical procedures. During a laparoscopic procedure, the operative field is viewed via a laparoscope which is inserted through one opening and the surgery is performed with instruments inserted through the other openings. Since the surgeon's hands remain outside of the patient during laparoscopic procedures, blunt dissectors, besides being used as dissectors, are also used to move organs into view for diagnostic purposes and into their proper anatomical positions following the procedure.

The use of conventional blunt dissectors, such as the peanut, during laparoscopic procedures presents many significant drawbacks. For instance, peanuts, being secured only by forceps, can become loose in the body. Further, the view of the operative field often becomes obstructed by pieces of tissue, blood and other bodily fluids produced during blunt dissection, necessitating the immediate need for both irrigation and aspiration of the operative field. Since it is undesirable to create additional incisions, the dissection must be stopped, the dissector must be removed, and an irrigator and/or aspirator must be inserted to remove the fluid and debris.

Others have attempted to overcome these drawbacks by developing blunt dissectors for use in laparoscopic procedures, but these new devices remain lacking. For example, combined irrigation-suction probes have been designed for performing blunt dissection during laparoscopic procedures, but these new probes have smooth, metal tips which are less effective as blunt dissectors than the textured surface of a peanut.

SUMMARY OF THE INVENTION

The laparoscopic irrigator-aspirator blunt dissector of the present invention overcomes the above mentioned drawbacks and disadvantages which are characteristic of the prior art. The blunt dissector of the present invention comprises an elongated suction tube for insertion into a trocar. A luer fitting, which is press fit over the proximal end of the suction tube, connects the suction tube to a source of irrigation fluid and to vacuum suction equipment. A cannulated mandrel, which has a reduced diameter portion, is press fit into the distal end of the suction tube, with the reduced diameter portion extending therefrom. Tightly wound around the reduced diameter portion of the mandrel is a strip of textured cloth containing an X-ray opaque thread. An inner tube is press fit within the cannulated bore of the mandrel and extends the full length of the mandrel such that a continuous internal bore is formed through the entire blunt dissector.

Numerous objects, features and advantages of the present invention will be readily apparent to those of ordinary skill in the art upon a reading of the following disclosure when taken in conjunction with the accompanying drawings.

DESCRIPTION OF THE PREFERRED EMBODIMENT

Figure 1:
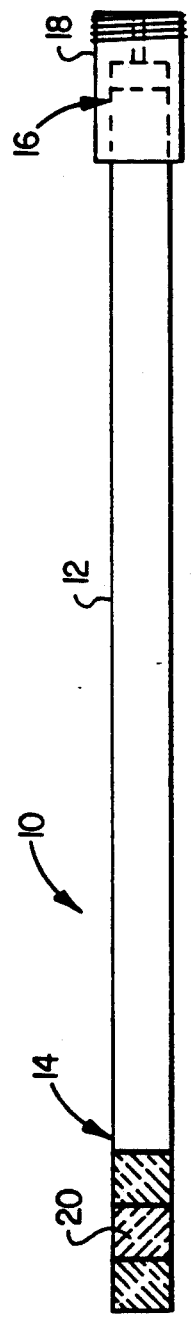
FIG. 1 is an elevational view of a blunt dissector according to the present invention.

Referring now to the drawings and particularly to FIG. 1, the blunt dissector of the present invention is shown and generally designated by the numeral 10.

The blunt dissector 10 includes an elongated tube 12, such as a stainless steel suction tube, having a distal end 14 and a proximal end 16. It will be recognized by those of ordinary skill in the art that the tube 12 may be formed from other materials such as titanium, hardened aluminum alloys, and plastic. The outer surface of the tube 12 is made nonreflective, thereby making it laser safe, by painting it with a nonreflective coating or by bead blasting to impart a dull finish.

A common luer fitting 18 which is press fit and secured over the proximal end 16 of the tube 12 connects the tube 12 to a source of irrigation fluid (not shown) and to vacuum suction equipment (not shown) in order to provide immediate irrigation and aspiration of the operative field, as needed. Since these types of connections are well-known, they will not be described in detail.

Figure 2:
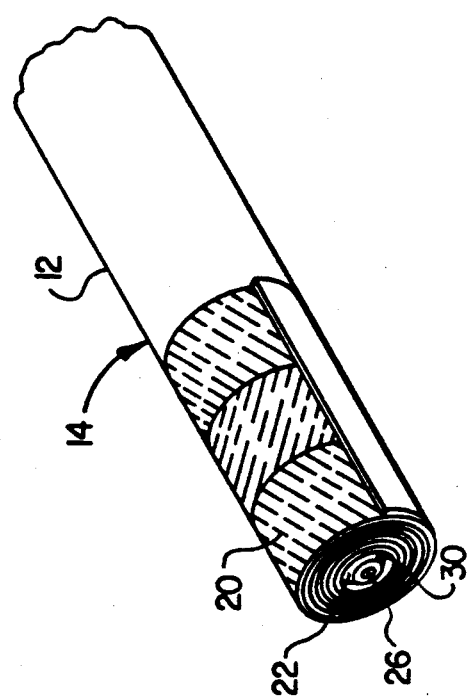
FIG. 2 is an enlarged perspective view of the dissector tip of the blunt dissector of the present invention.

Referring now to FIG. 2, the distal end 14 of the tube 12 is over wrapped with a strip of clot 20, the wrapping procedure for which is more fully described below. The cloth 20 preferably is textured so that the blunt dissector 10 can be used to pull and abrade the tissue being dissected. The cloth 20 should also be nonabsorbent to enable it to retain its stiffness, configuration and textured surface as it encounters bodily and irrigation fluids. Accordingly, the cloth 20 may be one or a mixture of polyester and rayon.

Figure 3:
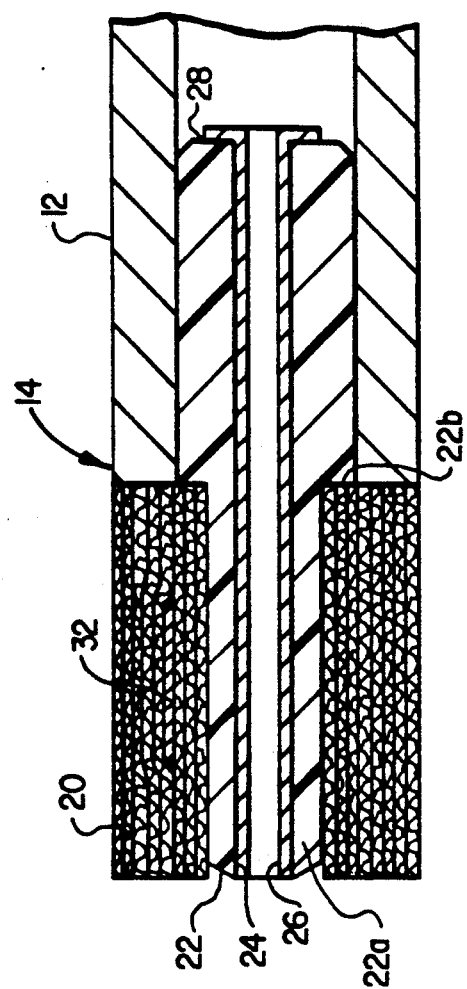
FIG. 3 is an enlarged sectional view of the dissector tip of the blunt dissector of the present invention.

Referring now to FIG. 3, press fit into the distal end 14 of the tube 12 is a mandrel 22 having a cannulated bore 24 and a reduced diameter portion 22a defining an outer shoulder 22b. The mandrel 22 is inserted into the tube 12 until the shoulder 22b aligns with the distal end 14 such that the reduced diameter portion 22a extends outwardly from the tube 12. The cloth 20 is wound around the reduced diameter portion 22a of the mandrel 22. The mandrel 22 preferably comprises nylon, but those of ordinary skill in the art will recognize that the mandrel 22 may comprise other suitable rigid plastics and composites as well as stainless steel or aluminum.

An inner tube 26, preferably cut from hypodermic needle stock, is press fit within the cannulated bore 24 and extends the full length of the mandrel 22. The bore of the inner tube 26 is in registry with the bore of the tube 12 so that a continuous internal bore is formed through the entire blunt dissector 10. The inner tube 26 is flared at an end 28 of the mandrel 22 to prevent the dislodgement of the inner tube 26 from the mandrel 22.

An axial slit 30 is formed along the entire length of the reduced diameter portion 22a of the mandrel 22 to facilitate the winding of the cloth 20. An end of the cloth 20 is inserted into the slit 30 and pinned between the inner tube 26 and the mandrel 22 to firmly secure the cloth 20 to the mandrel 22. In a prefered embodiment, a small amount of a convential medical grade adhesive is applied to the portion of the cloth 20 immediately extending from the axial slit 30 to further secure the cloth 20 to the mandrel 22. The cloth 20 is then wound tightly around the reduced diameter portion 22a of the mandrel 22 such that the cloth 20 abuts the shoulder 22b and the distal end 14 of the tube 12. During the course of the winding operation, a small thread 32 of X-ray opaque material, which preferably includes barium, is positioned traversing the cloth 20, so that as the cloth 20 is wound, the thread 32 becomes securely contained within the wound cloth. The cloth 20 preferably is heat welded after the winding operation to secure the cloth 20 on the mandrel 22.

In operation, the distal end 14 of the blunt dissector 10 is inserted into an operative field via a laparoscopic trocar. While viewing the operative field through a laparoscope, the distal end 14 is maneuvered to an area of tissue to be dissected. If the tissue must be penetrated, it can be punctured with the tip of the blunt dissector 10 and the opening can be widened by abrading the perimeter of the opening with the rolled cloth 20. If the tissue must be removed from the exterior of an organ or the like, the cloth 20 may be rubbed over the tissue so that the tissue will be grabbed by the textured surface of the cloth 20. The tissue can then be pulled away from the organ by retracting the blunt dissector 10.

When irrigation of the operative field is required, irrigation fluid is introduced, via the luer fitting 18, into and through the continuous bore defined by the tube 12 and the inner tube 26. The fluid discharges through the inner tube 26 and into the operative field at a relatively high velocity to irrigate the area and cleanse it of debris. Then, to aspirate the operative field, the vacuum-suction equipment (not shown) is engaged to provide suction at the distal end 14 of the tube 12. The unwanted fluid and debris is drawn, via the inner tube 26, into the continuous bore defined by the tube 12 and the inner tube 26, and out of the blunt dissector 10 via the luer fitting 18.

It is thus seen that the blunt dissector 10 of the present invention provides several advantages. In general, the blunt dissector 10 allows for laparoscopic blunt dissection while having the simultaneous capability to irrigate and/or aspirate the operative field, thereby offering the ability to cleanse the operative field of blood and debris, as well as smoke from laser dissection, without having to cease dissection or change instrumentation.

More particularly, the blunt dissector 10 provides greater effectiveness as a laparoscopic blunt dissector than prior art devices due to the textured surface of the cloth 20. In addition, the blunt dissector 10 of the present invention provides a safer means of performing blunt dissection in general since the cloth 20 used to perform the dissection is securely attached to the instrument, thereby preventing its dislocation into the patient.

Further, due to the inclusion of the barium thread 32, if the cloth 20 becomes dislodged from the blunt dissector 10 and drops into the operative field, it can be located and retrieved by directing a beam of X-rays through the patient.

Besides its primary function of being a blunt dissector with the capability to irrigate and aspirate the operative field, the blunt dissector 10 of the present invention can also supply other needed functions. The blunt dissector 10 is an effective instrument for moving organs during laparoscopic procedures, such as to place them in view for diagnostic purposes or back into their proper anatomical positions following surgery. Significantly, the blunt dissector 10 can also be used to perform aqua dissection due to its irrigation ability. Additionally, the blunt dissector 10 can also be used during adhesiolysis, endoscopic procedures, and even during normal surgical procedures.

It is understood that variations may be made in the foregoing description of the blunt dissector 10 without departing from the scope of the present invention. For example, the blunt dissector has been described as being comprised of a suction tube, a mandrel, an inner tube and a wound cloth. Alternatively, certain of the components, such as the suction tube, mandrel and inner tube, can be formed as a single piece.

Other modifications, changes and substitutions are intended in the foregoing disclosure and in some instances some features of the present invention will be employed without a corresponding use of other features. Accordingly, it is appropriate that the appended claims be construed broadly and in a manner consistent with the scope of the invention.

What is claimed is:

1. A medical instrument, comprising:
   an elongated tube having a first end, a second end and a bore extending between said first end and said second end;
   means for connecting said first end of said tube to means for passing fluid through said tube;
   textured means for dissecting tissue disposed at said second end of said tube; and
   a cannulated mandrel having a first end disposed within said second end of said tube and a second end extending form said second end of said tube, wherein said textured means for dissecting tissue is disposed on said second end of said mandrel.

2. The medical instrument of claim 1, wherein said textured means for dissecting tissue is wound about said second end of said mandrel.

3. The medical instrument of claim 2, wherein said textured means for dissecting tissue is nonabsorbent.

4. The medical instrument of claim 2, wherein said textured means for dissecting tissue comprises a member selected from the group consisting of polyester, rayon and mixtures thereof.

5. The medical instrument of claim 2, further comprising a strip of X-ray opaque material disposed within said textured means for dissecting tissue.

6. The medical instrument of claim 1, further comprising an inner tube having a bore, said inner tube extending within said mandrel, wherein said bore of said inner tube registers with said bore of said elongated tube.

7. The medical instrument of claim 1, wherein said inner tube comprises hypodermic needle stock.

8. The medical instrument of claim 1, further comprising X-ray opaque material disposed at said second end of said elongated tube.

* * * * *

UNITED STATES PATENT AND TRADEMARK OFFICE
CERTIFICATE OF CORRECTION

PATENT NO. : 5,205,816

DATED : April 27, 1993

INVENTOR(S) : Donald Dodson et al.

It is certified that error appears in the above-identified patent and that said Letters Patent is hereby corrected as shown below:

Column 2, line 63, change "clot" to -- cloth --.

Signed and Sealed this

Fourth Day of January, 1994

Attest:

BRUCE LEHMAN

*Attesting Officer*     *Commissioner of Patents and Trademarks*